United States Patent [19]
Smith et al.

[11] Patent Number: 5,753,439
[45] Date of Patent: May 19, 1998

[54] NUCLEIC ACID DETECTION METHODS

[75] Inventors: Cassandra L. Smith, Boston; Ron Yaar, Brookline; Przemyslaw Szafranski; Charles R. Cantor, both of Boston, all of Mass.

[73] Assignee: Trustees of Boston University, Boston, Mass.

[21] Appl. No.: 446,102

[22] Filed: May 19, 1995

[51] Int. Cl.$^6$ .............................. C12Q 1/68; C12Q 1/70; C12P 19/34; C07H 21/04

[52] U.S. Cl. .................. 435/6; 435/5; 435/91.2; 536/24.3; 536/24.32; 536/24.33

[58] Field of Search .................. 435/6, 5, 91.2; 536/24.3–24.33, 26.6

[56] References Cited

U.S. PATENT DOCUMENTS

| | | | |
|---|---|---|---|
| 4,946,773 | 8/1990 | Maniatis et al. | 435/6 |
| 5,032,502 | 7/1991 | Stodolsky | 435/6 |
| 5,175,082 | 12/1992 | Jeffreys | 435/6 |
| 5,376,526 | 12/1994 | Brown et al. | 435/6 |
| 5,459,039 | 10/1995 | Modrich et al. | 435/6 |

FOREIGN PATENT DOCUMENTS

| | | |
|---|---|---|
| 0259031 | 3/1988 | European Pat. Off. |
| 0497272 | 8/1992 | European Pat. Off. |
| WO8703911 | 7/1987 | WIPO |
| WO9115600 | 10/1991 | WIPO |
| WO9210588 | 6/1992 | WIPO |
| WO9322462 | 11/1993 | WIPO |
| WO9428175 | 12/1994 | WIPO |
| WO9521269 | 8/1995 | WIPO |

OTHER PUBLICATIONS

Yee and Inouye. PNAS 81: 2723–2727, 1984.

Rampal et al. Clinical Chemistry 40(12):2337 Dec. 19, 1994.

Beattie et al. Clinical Chemistry 41/5: 700–706 (of interest), 1995.

Chetverin and Kramer Biotechnology 12: 1093–1098, 1994.

C., Thomas Caskey et al., "Triplet Repeart Mutations in Human Disease." *Science*, vol. 256, May 8, 1992, pp. 784–789.

David L. Nelson et al., "Trinucleotide Repeat Instability: When and Where?" *Nature Genetics*, vol. 4, Jun. 1993, pp. 107–108.

Christopher A. Ross et al., "Genes with Triplet Repeats: Candidate Mediators of Neuropsychiatric Disorders," *TINS*, vol. 16, No. 7, 1993, pp. 254–260.

Robert I. Richards et al., "Dynamic Mutations: A New Class of Mutations Causing Human Disease." *Cell*, vol. 70, Sep. 4, 1992, pp. 709–712.

Grant R. Sutherland et al., "Simple Tandem DNA Repeats and Human Genetic Disease." *Proc. Natl. Acad. Sci. USA*, vol. 92, Apr. 1995, pp. 3636–3641.

M.S. Wehnert et al., "A rapid scanning strip for tri-and dinucleotice short tandem repeats", *Nucleic Acids Research*, (1994), vol. 22, No. 9, pp. 1701–1704.

*Primary Examiner*—W. Gary Jones
*Assistant Examiner*—Dianne Rees
*Attorney, Agent, or Firm*—James Remenick; Baker & Botts, L.L.P.

[57] ABSTRACT

The invention relates to methods for rapidly determining the sequence and/or length a target sequence. The target sequence may be a series of known or unknown repeat sequences which are hybridized to an array of probes. The hybridized array is digested with a single-strand nuclease and free 3'-hydroxyl groups extended with a nucleic acid polymerase. Nuclease cleaved heteroduplexes can be easily distinguish from nuclease uncleaved heteroduplexes by differential labeling. Probes and target can be differentially labeled with detectable labels. Matched target can be detected by cleaving resulting loops from the hybridized target and creating free 3-hydroxyl groups. These groups are recognized and extended by polymerases added into the reaction system which also adds or releases one label into solution. Analysis of the resulting products using either solid phase or solution. These methods can be used to detect characteristic nucleic acid sequences, to determine target sequence and to screen for genetic defects and disorders. Assays can be conducted on solid surfaces allowing for multiple reactions to be conducted in parallel and, if desired, automated.

58 Claims, 7 Drawing Sheets

FIG. 1A
A
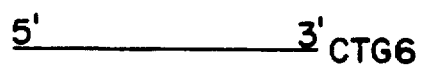
ANNEAL
FIG. 1B
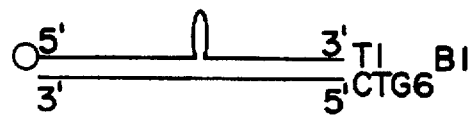
CUT WITH S1 NUCLEASE
C
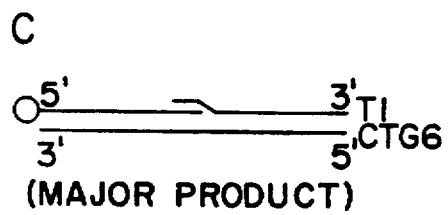
(MAJOR PRODUCT)
D
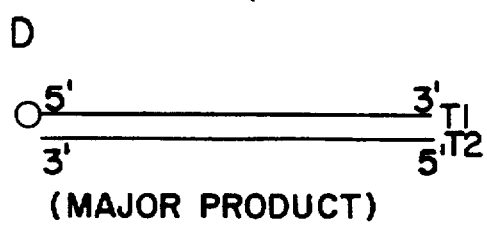
(MAJOR PRODUCT)
FIG. 1D
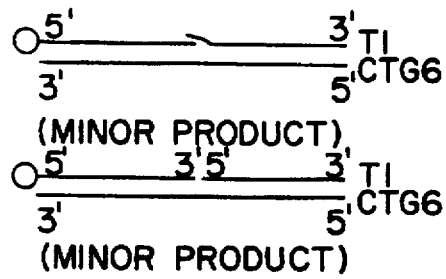
(MINOR PRODUCT)
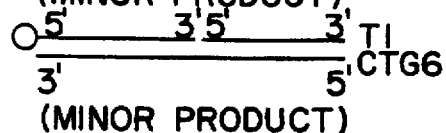
(MINOR PRODUCT)
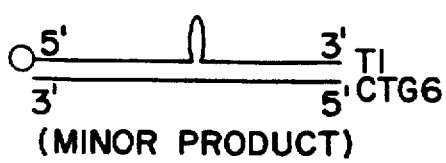
(MINOR PRODUCT)
FIG. 1C (MAJOR PRODUCT)

(MINOR PRODUCT)

(MINOR PRODUCT)

A (MAJOR PRODUCT)

(MINOR PRODUCT)

KLENOW FRAGMENT (MAJOR PRODUCT)

B (MAJOR PRODUCT)

(MINOR PRODUCT)

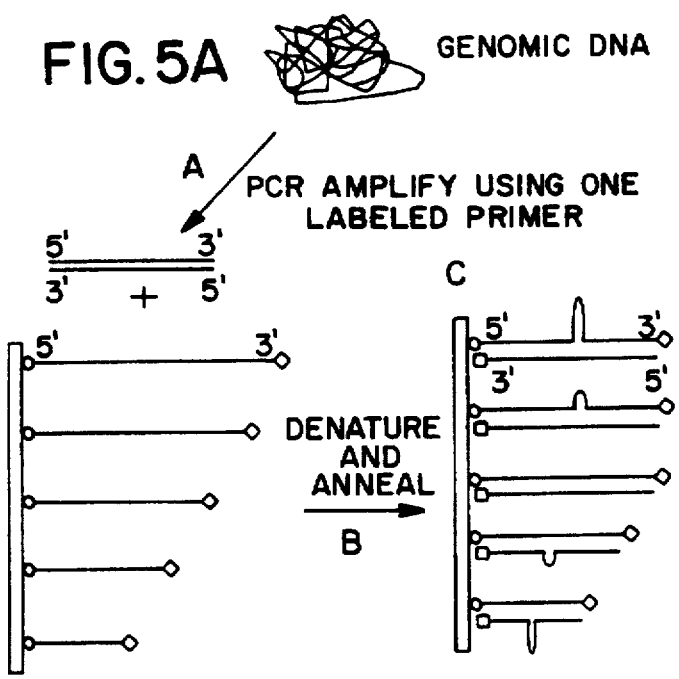
FIG. 5A
FIG. 5B
FIG. 5C
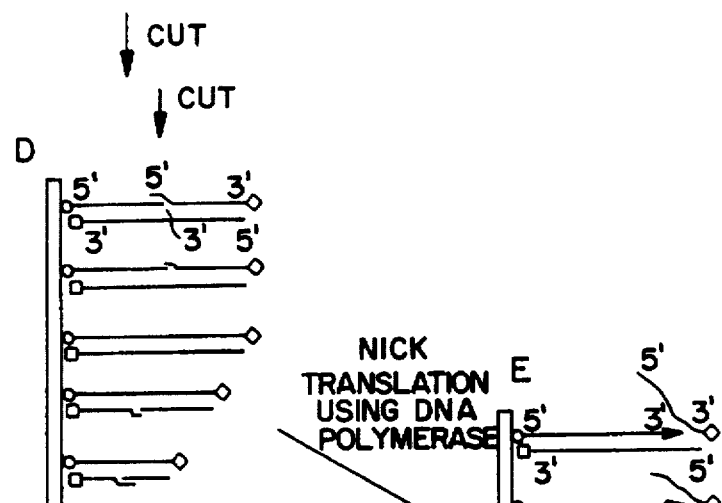
FIG. 5D
FIG. 5E
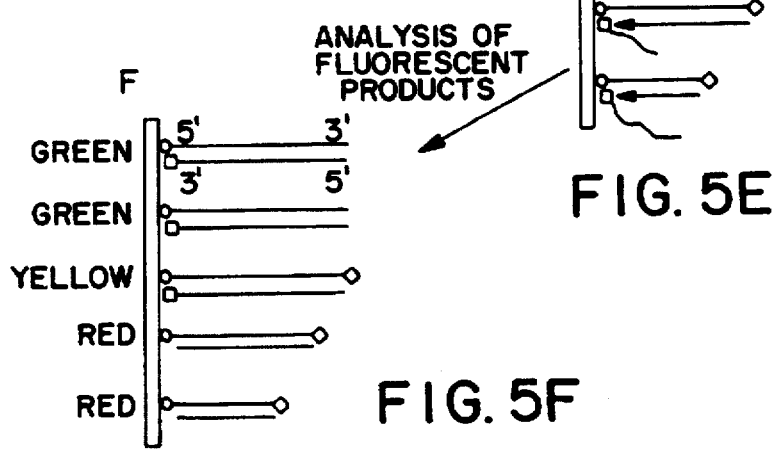
FIG. 5F

*S1 cutting and strand displacement*

NUCLEIC ACID DETECTION METHODS

RIGHTS TO THE INVENTION

This invention was made with United States Government support under grant number DE-FG02-93ER61609, awarded by the United States Department of Energy, and grant number AIBS2154, awarded by the United States Department of the Army, and the United States Government has certain rights in the invention.

BACKGROUND OF THE INVENTION

1. Field of the Invention

This invention relates to methods for the detection of repeated and other identifiable nucleic acid sequences. The invention also relates to methods for identifying and mapping specific nucleic acid sequences in complex backgrounds.

2. Description of the Background

Historically, the diagnosis of genetic disease has depended on the identification of abnormal gene products or their clinical effects such as anemia, mental retardation and certain schizophrenia. Through direct analysis of the genome, it is possible to identify genetic mutations and offer treatment before the manifestation of symptoms. Genetic analyses performed today range from gross analysis such as karyotyping to the analysis of individual base pairs by sequencing. Although a great deal of progress has been made, nucleic acid sequencing is still too labor intensive and expensive for everyday diagnosis beyond the experimental medical research laboratory.

Many genetic defects such as Burkett's lymphoma and some sickle cell anemia and thalassemia mutations are detectable without the use of sequencing. Such techniques include restriction fragment length polymorphism (RFLP) and chromosome karyotyping. However, general applicability of these methods is limited as most genetic defects are more modest and do not alter restriction sites or cause chromosome rearrangements. Polymerase chain reaction and ligase chain reaction can increase the sensitivity of many detection methods and detect single base pair changes in nucleic acid. However, if the mutation involves repeated sequences, the degeneracy of the repeated sequence makes even PCR and LCR detections unreliable.

Dinucleotide and trinucleotide repeat sequences are increasingly becoming important in genetic analysis. These repeats are both polymorphic and widespread in the human genome and offer a convenient means for locating genes associated with particular phenotypes (M. S. Wehnert et al., Nuc. Acids Res. 22:1701–4, 1994; G. Benson et al., Nuc. Acids Res. 22:4828–36, 1994).

Trinucleotide repeat expansion mutations have been identified in at least four human genetic diseases (C. T. Caskey et al., Sci. 256:784–89, 1992). Each are caused by mutational mechanisms whereby normally polymorphic exonic trinucleotide repeats expand beyond the normal size range and alter gene expression, mRNA stability or gain certain functions. In Fragile X syndrome (FraX; D. L. Nelson et al., Nature Genetics 4:107–108, 1993), the second most common genetic form of mental retardation, and also in myotonic dystrophy (MD; D. J. Brook et al., Cell 68:799–808, 1992), the repeat expansion can be quite large resulting n thousands of triplets. In spinal and bulbar muscular atrophy (SBMA or Kennedy disease) and Huntington's Disease (HD), the expansion may only consist of twice the normal compliment of repeats.

The genetic element expanded in Fragile X is a triplet called FMR-1. This sequence, CGG, is highly polymorphic in the general population ranging from between about 6 to about 42 triplets per person. Unaffected family members can contain up to 50 repeats. Between 50 and 200, individuals are considered to be pre-mutation. Expansions of several thousand are known to occur in affected patients.

Myotonic dystrophy is an autosomal dominant disorder characterized by muscle weakness and is the single-most common form of adult onset. The gene responsible, DM-1 has been identified There are many methods for detecting differences in repeat number. Conventional analyses involve electrophoretic fractionation steps. Such steps are seriously limiting in terms of time and expense and lack the sensitivity for detecting short deletions in long sequences (M. B. White et al., Genomics 5:301–6, 1992). Chemical detection and cleavage of mismatches, though effective, generally relies on the use of dangerous compounds (P. M. Smooker et al., Mutant. Res. 288:65–77, 1993). The advent of efficient coupling of DNA to solid surfaces as well as progress in effective florescent labeling and detection have paved the way for the development of assays able to determine the length of these dinucleotide and trinucleotide repeats quickly and accurately.

SUMMARY OF THE INVENTION

The invention overcomes the problems and disadvantages associated with current strategies and designs and provides novel methods for the detection and identification of nucleic acid sequences and novel arrays which can be utilized with these methods.

One embodiment of the invention is directed to methods for detecting a target sequence within a nucleic acid. The nucleic acid is hybridized to an array of probes wherein each probe comprises a 5'-region complementary to the nucleic acid, a 3'-region complementary to the nucleic acid, and an internal variable region. The hybridized array is digested with a single-strand specific nuclease and treated with a nucleic acid polymerase. The target sequence may vary in length or sequence, for example, comprising a plurality of short repeat sequences or a homologous sequence of bases of variable lengths. The sequence and length of the target can be identified by hybridization to a specific probe and resistance to the single-strand specific nuclease.

Another embodiment of the invention is directed to methods for determining the length of a target sequence within a nucleic acid. A nucleic acid is hybridized to an array of probes wherein each probe comprises a 5'-region complementary to the nucleic acid, a 3'-region complementary to the nucleic acid, and an internal variable region. The hybridized array is digested with a single-strand specific nuclease and treated with a nucleic acid polymerase. The nucleic acid may be a PCR product, such as an amplified nucleic acid sequence, or a DNA or RNA macromolecule purified, if necessary, directly from a biological sample. The internal variable region may comprises a homologous sequence of bases such as a sequence inosine residues which non-specifically hybridize to nucleic acids. Hybridized probes resistant to nuclease digestion will be the same length as the target sequence.

Another embodiment of the invention is directed to methods for determining the number of repeat sequences within a nucleic acid. The nucleic acid is hybridized to an array of probes wherein each probe comprises a 5'-region complementary to the nucleic acid, a 3'-region complementary to the nucleic acid, and an internal region which contains one or more repeat sequences. The hybridized array is digested with a single-strand specific nuclease and treated with a nucleic acid polymerase. Hybridized probes resistant to the nuclease digestion contain the same number of repeats as the target sequence.

Another embodiment of the invention is directed to methods for screening a patient suspected of having a genetic disorder. A tissue sample is obtained from the patient and a nucleic acid sequence obtained by, for example, PCR amplification or direct purification of a target sequence. The nucleic acid is hybridized to an array of probes wherein each probe comprises a 5'-region and a 3'-region, each complementary to the nucleic acid and a variable internal region. The hybridized array is digested with a single-strand specific nuclease and treated with a nucleic acid polymerase. Hybridized probes resistant to nuclease digestion will contain a specific number of repeat sequences. The presence or absence of the genetic disorder can be determined from the number of repeat sequences which are present.

Another embodiment of the invention is directed to arrays of probes wherein each probe comprises a constant 5'-region, a constant 3'-region and a variable internal region wherein the variable region comprises one or more repeat sequences. The repeat sequence comprises heterologous or homologous sequences which are variable in length or base sequence. Sequences contain purine or pyrimidine bases or neutral bases such as inosine. Either the nucleic acids or the probes of the array may be labeled with a detectable label or fixed to a solid support.

Other embodiments and advantages of the invention are set forth, in part, in the description which follows and, in part, will be obvious from this description and may be learned from the practice of the invention.

DESCRIPTION OF THE DRAWINGS

FIG. 1A–D Schematic of the reaction strategy.

FIG. 5A–F Scheme for detection of mismatches using anchored single-stranded oligonucleotide probes.

DESCRIPTION OF THE INVENTION

Figure 2A:
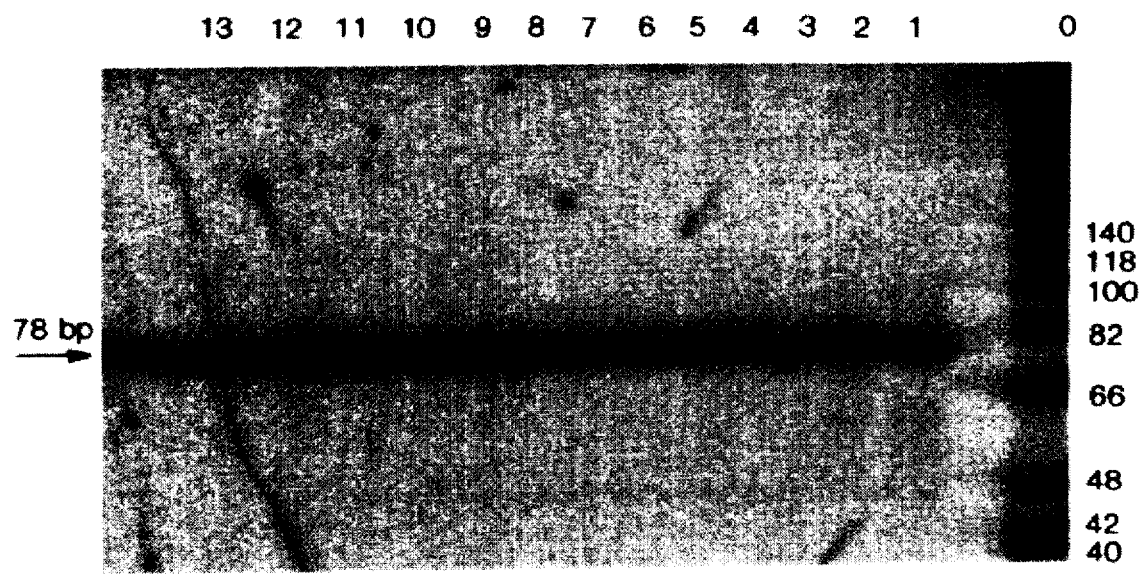
FIG. 2A and B Results of mismatch cleavage with S1 nuclease.

As embodied and broadly described herein, the present invention is directed to methods for the detection and identification of target sequences by size or base sequence and to arrays of nucleic acid probes which can be utilized with these methods.

Nucleic acid screening is widely utilized to detect and identify nucleic acids. The presence or absence of these specific nucleic acids, as identified by their sequences, can often be considered as evidence of disorders such as infections, neoplasms and genetic diseases. Although there are a wide variety of methods currently available, sequence detection is generally a slow and expensive proposition requiring costly supplies and the skills of highly trained individuals.

It has been discovered that by combining certain microchemical tools such as nucleic acid probes, nucleic acid hybridization and enzymatic cleavage of heteroduplexed hybrids, procedures can be designed to detect specific target sequences. Characteristic sequences such as occurs in variations between strains of microorganisms and between numbers of repeat sequences can be rapidly and accurately detected and identified.

Nucleic acids containing these target sequences can be hybridized to oligonucleotide probes that contain sequence variations such as a different repeat lengths. Loop structures formed by mismatched repeats can be cleaved by incubation with a nuclease to generate nicked double strands. These nicks are recognized by a nucleic acid polymerase which breaks down or displace one of the strands. Analysis of the products using, for example, differential labeling, reveals the nature of the mismatch as well as the length of the perfectly matched repeats. As reactions can be conducted in situ and all under the same conditions, process steps can be easily automated. Many assays could be run in parallel allowing for rapid analysis of target sequence from a variety of sources.

One embodiment of the invention is directed to a method for detecting a target sequence within a nucleic acid. Nucleic acids containing target sequences to be detected can be obtained directly or indirectly from natural or synthetic sources. Synthetic sources include sequences chemically synthesized such as oligonucleotides or sequences of PNA. Natural sources of nucleic acid sequences include samples of bodily tissues or fluids obtained from a patient, samples from the environment such as a biomass, soil or body of water. Nucleic acids directly obtained from such sources can be purified, if necessary, by techniques such as centrifugation, chromatography, chemical extraction, precipitation or other techniques or combinations of techniques known to those of ordinary skill in the art. As sequence information is easily transcribed or replicated, the nucleic acid may be either RNA or DNA and may exist in either the sense or anti-sense orientation.

Nucleic acids are preferably single-stranded, but may be partially single-stranded and partially double-stranded. Single-stranded regions hybridize to probe sequences and double-strand regions can contain recognitions sites for restriction enzymes or other nucleic acid modifying enzymes sites, or used to chemically couple detectable labels. If necessary, single-stranded nucleic acids can easily be prepared from target sequences by a number of methods. The strands of most double helixes, once denatured by treatment with 8 M urea, low or high pH or 95° C. heat, can be separated by, for example, denaturing electrophoresis. Alternatively, polymerase chain reaction using one or an excess of one primer may be performed using the target sequence as a template causing the product to consist mainly of one strand. Elongation products formed, for example, using a biotinylated primer can be isolated with a streptavidin column. mRNA, or single stranded cDNA may also be isolated and used as a single stranded target.

The nucleic acid containing the target sequence is preferably generated as a polymerase chain reaction (PCR) product. The basic PCR process is described in U.S. Pat. No. 4,683,195. Variations of the PCR process are described in U.S. Pat. Nos. 5,043,272, 5,057,410 and 5,106,727. As a PCR product, the nucleic acid will possess both 5' and 3' terminal sequences which are identical to the sequences of the primers used in the PCR reaction. These primers flank the sequence to be amplified which comprises the target sequence. Primers are typically less than about 35 nucleotides in length, but may be smaller or larger as necessary to generate the nucleic acid. Although not required, the sequences of the primers are generally known for the primers to specifically hybridize to a relatively unique portion of nucleic acid and generate an identifiable nucleic acids on PCR amplification. PCR products can be of most any length and can be distinguished from non-specific and undesired amplification products by size.

In PCR and any polymerase amplification procedure, extensions may be added to the 5'-termini of a primer to permit post-amplification manipulations of the product without significantly effecting the amplification reaction. These 5' extensions may be restriction enzyme recognition sites, structural sequences or other sequences desirable for the process. Briefly, template DNA is first denatured by heating in the presence of a large molar excess of each of the two oligonucleotides and the four dNTPs. The reaction mixture is cooled to a temperature that allows the oligonucleotide primer to anneal to target sequences, after which the annealed primers are extended with DNA polymerase. The cycle of denaturation, annealing, and DNA synthesis, the principal of PCR amplification, is repeated many times to generate large quantities of product which can be easily identified. This temperature cycling is made possible by the use of a DNA polymerase that does is not destroyed at the higher temperatures required for denaturation. Nucleic acid polymerases which can be used for amplification include both DNA and RNA polymerases. Many useful thermostable polymerases for PCR amplification are commercially available such as Taq DNA polymerase (Stratagene; La Jolla, Calif.) and AMPLITAQ DNA polymerase (Perkin-Elmer Cetus; Norwalk, Conn.).

The major product of this exponential reaction is a segment of double stranded nucleic acid, easily converted to single strands by, for example, chemical, pH or heat denaturation, whose termini are defined by the 5' termini of the oligonucleotide primers and whose length is defined by the distance between the primers. Under normal reaction conditions, the amount of polymerase becomes limiting after 25 to 30 cycles or about one million fold amplification. Further amplification is achieved by diluting the sample 1000 fold and using it as the template for further rounds of amplification in another PCR. By this method, amplification levels of $10^9$ to $10^{10}$ can be achieved during the course of 60 sequential cycles. This allows the detection, by hybridization with radioactive probes, of a single copy of the target sequence in the presence contaminating DNA. Without the use of sequential PCR, the practical detection limit of PCR can be as low as 10 copies of DNA per sample.

Although PCR is a reliable method for amplification of target sequences, a number of other techniques can be used such as isothermic amplification, ligase chain reaction (LCR), self sustained sequence replication (3SR), polymerase chain reaction linked ligase chain reaction (pLCR), gaped ligase chain reaction (gLCR), ligase chain detection (LCD). The principle of ligase chain reaction is based in part on the ligation of two adjacent synthetic oligonucleotide primers which uniquely hybridize to one strand of the target DNA or RNA. If the target is present, the two oligonucleotides can be covalently linked by ligase. A second pair of primers, almost entirely complementary to the first pair of primers is also provided in a ligase chain reaction. In a ligase chain reaction, the template and the four primers are placed into a thermocycler with thermostable ligase. As the temperature is raised and lowered, oligonucleotides are renatured adjacent to each other on the template and ligated. The ligated product of one reaction serves as the template for a subsequent round of ligation. The presence of target is manifested as a DNA fragment with a length equal to the sum of the two adjacent oligonucleotides. Additional PCR variations include in situ PCR and immuno-PCR amplification which utilizes nucleic acid fragments coupled to pathogen-specific antibodies to increase detection sensitivity. Alternatively, nucleic acids can be analyzed after purification using, for example, DNA or RNA polymerases, PCR or another amplification technique. PCR analysis of RNA, or RT-PCR, involves reverse transcription of RNA, such as mRNA sequences, into cDNA copies. These target cDNA sequences are hybridized to primers which amplify the nucleic acid using PCR amplification.

Although high level amplification may be possible, it may not always be necessary or even desired when, for example, the sequence amplified is likely to mutate or otherwise be altered during the amplification process. In such cases, PCR can be limited to just a few rounds of amplification or avoided altogether and sequence replicated using more conventional nucleic acid polymerases.

The sequence of the nucleic acid including the target sequence will be determined by the sequence of the nucleic acid obtained from the sample. However, synthetic sequences may be added or the entire nucleic acid may be synthetically synthesized. As such, nucleic acids may comprise any combination of purines or pyrimidines, modifications or derivatives of purines or pyrimidines, or other chemical moieties which can be hybridized specifically or non-specifically to a nucleic acid sequence. For example, neutral bases, those bases which non-specifically hybridize to most any other base, such as inosine or modifications or derivatives of inosine, can be incorporated. In addition, incorporation of residues such as thiolated bases, boronated bases, polyamides and peptide nucleic acids can produce sequences which are resistant to enzymatic degradation.

Sequences of the nucleic acid, including the target sequence, may encode protein or be entirely non-coding sequences such as structural sequences or sequences which regulate expression. Structural sequences include ribosomal RNA and telomeres. Controlling sequences include promoter sequences, enhancers, 5'- and 3'-untranslated sequences and sequences that function outside of expression such as ribozymes. Identification of variations within such sequences can be important in determining treatment regiments, such as in identifying repeat numbers, in determining molecular structure and in generating relationships. For example, target sequences within the nucleic acid may be sequences which are specific to a particular species or strain of organism such as a bacterium, virus, parasite or fungus, or the sequence of a translated or untranslated portion of a eukaryotic or prokaryotic gene. Identification of such sequences can be used to detect and often identify the organism. Alternatively, the target sequence may comprise a homologous sequence such as inosine, uracil (U) or deoxyuracil (dU), when only the length of the target sequence is to be determined.

Nucleic acids are hybridized to an array of probes by any number of techniques known to those of ordinary skill in the art. For example, hybridizations may be performed in a buffered salt solutions such as SSC (3M NaCl, 0.3 M Na Citrate, pH 7.0), or SSPE (3M NaCl, 0.2 M Na Phosphate, 0.02 M EDTA, pH 7.4). Other solutions can be utilized where melting temperature of the double helix is independent of base composition and dependent only on length. Solutions which have this property include solvents containing quaternary alkylammonium salts such as solutions of tetramethyl-ammonium chloride or tetraethylammonium chloride. In quaternary alkylammonium solutions the bonding strength of AT base pairs and GC base pairs are approximately the same.

Probes of the array each comprise regions which are complementary to one or more portions of the nucleic acid. Preferably, probes comprise 5'-region and 3'-regions which are complementary to portions of the nucleic acid and an internal variable region. The variable region can vary in sequence and/or length and, preferably, one of the variable region sequences of the array is complementary to or will otherwise completely hybridize to the target sequence. Variations in probe sequence will prevent certain of the probes from fully hybridizing to the nucleic acid containing the target sequence. These heteroduplexed probes, containing an unhybridized portion in either the probe or the nucleic acid, are susceptible to digestion using a single-strand specific nuclease.

Probes and nucleic acids may be identically or differentially labeled with detectable labels. Detectable labels include radio-isotopes such as $^{125}I$, $^{35}S$, $^{32}P$ or $^{3}H$, stable-isotope or chemical moieties such as a fluorescent, luminescent or chemiluminescent compounds. Additional labels which may be used include chromogenic chemicals, metals, coupling agents such as biotin/streptavidin or avidin, mass modifying moieties, magnetic agents or chemicals detectable by nuclear magnetic resonance or electron spin resonance. Labels may be incorporated enzymatically, for example, during generation of the nucleic acid or by chemical modification of the final structure. Specifically useful labeling compounds are those which do not interfere with the polymerase reaction such as rhodamine, fluorescein, dansyl chloride, coumarin, digoxin, fluorescamine and derivatives and modifications of these compounds.

Probes or target nucleic acids may also be fixed to a solid support or free in solution. When free in solution, hybridization may be in an ordered fashion such as in well separated wells of a microtiter dish or multi-well chip, or together in a single well or small number of wells. In this fashion, batch analysis of hybrids can be performed sequentially to minimize the number of probes needed to identify an unknown target sequence. Alternatively, probes can be hybridized to nucleic acids in an ordered fashion such that individual hybridization events can be accurately scored. Useful solid supports include plastics, glasses, ceramics, metals, resins, gels, membranes, chips such as hybridization chips, and combinations of these materials and structures.

This hybridized array, either fixed or free in solution, is digested with a single-strand specific nuclease to cleave single stranded regions such as heteroduplexes and terminal extensions. Nucleases suitable for digestion of hybridized probes include those nuclease which preferentially cleave single-stranded nucleic acids. Preferred nucleases include the endonucleases such as S1 nuclease, mung-bean nuclease, ribonuclease A and ribonuclease T1. Nucleic acids or probes which generate terminal single strands can be digested with exonucleases such as the T4 and T7 phage nucleases. When desired, treatment with excess nuclease can be directed to produce double-stranded cleavage by extending the nick to a gap and thereby creating a single-stranded region on the opposite strand. Such double-stranded cuts can be useful in procedures where probes are fragmented.

Nicked hybrids can be labeled using terminal deoxytransferase or another suitable nucleic acid modifying enzyme, and precursor dNTPs or ddNTP detectably labeled with a radio isotope, stable-isotope or chemical moiety such as a fluorescent, luminescent or chemiluminescent moiety. Additional labels which may be incorporated include chromogenic chemicals, metals, coupling agents such as biotin/streptavidin or avidin, mass modifying moieties, magnetic agents or chemicals detectable by nuclear magnetic resonance or electron spin resonance.

Digested hybridized probes are then contacted with a nucleic acid polymerase to extend nicked strands and thereby displace one strand of the heteroduplex. Polymerases which can be used for elongation include any polymerase which can elongate a template after a nick. Most DNA polymerase of most organisms are suitable for the practice of this invention. Examples of suitable polymerase include human DNA polymerase I, II, and III, E. coli DNA polymerase I, II, and III, T7, T3, and SP6 polymerase, thermostable DNA polymerase, sequenase, and amplitaq polymerase.

Another embodiment of this invention is directed to a method to measure the length of a target sequence. Probes constructed for length measurements preferably comprise neutral bases such as inosine residues flanked by two constant region sequences. An advantage of neutral bases in that a knowledge of the target sequence is not required. Neutral base forms stable base pairs with all four conventional bases and the strength of the paring is approximately equal in each case. With the use of a neutral base, the assay will be sensitive only to the length, but not the sequence of the target.

Another embodiment of the invention is directed to a method for detecting the number of repeat sequences in a target nucleic acid. A target sequence may be from a natural source or a synthetic source. Natural sources of target sequence may include DNA, and RNA from an organism. The nucleic acid may be from sequences which encodes a protein, such as exons and mRNA. The nucleic acid may also be from structural and from non-coding sequences such as ribosomal RNA, and telomeres. Genes which comprise repeated sequences, such as human TFIID and human DNA polymerase II largest subunit, have internal trinucleotide repeats which encodes for strings of homopeptides whose length varies between individuals. Non coding repeat sequences include the repeating DNA and telomeric sequences. Synthetic sources of nucleic acids may be from a laboratory reaction, a nucleic acid synthesis machine. Additional sources of nucleic acids may be from nucleic acids added to industrial and consumer goods.

To determine the number of repeats in a target sequence, the target sequence is hybridized to a plurality of probes, each containing none, one or more than one repeat. Where the number of repeats in the target do not correspond to the number of repeats in the probe, one or more single stranded loop can be present on the target-probe hybrid. Single stranded loops are only absent in the hybrid with a perfect match. Perfect matches constitute hybrids of nucleic acid target to probes with the same number of repeats. Single strand nuclease treatment after hybridization will digest all the single stranded loops leaving nicked hybrids and un-nicked hybrids. Polymerase treatment after digestion elongates and displaces strands of all nicked hybrids. Hybrids with a perfect match and without nicks will be the only hybrids not affected by polymerase. By monitoring the polymerase reaction, the hybrid with the perfect match can be identified and the number of repeats in the target can be determined.

The polymerase reaction can be monitored by a number of methods. The polymerase elongation reaction may be performed in the presence of nucleotide triphosphates with a detectable moiety. On detectable moiety is a radio-label such as $^{32}P$ or $^{35}S$ on the α-phosphate. All the hybrids with an incorrect number of repeated sequence will be labelled while the hybrid with equal number of repeats will remain unlabeled. Thus, the assay allows for the precise identification of the number of bases or the number of repeat sequences in a target sequence. As such, these methods are faster and more sensitive than methods currently available.

Another embodiment of the invention is directed to a method for screening a patient suspected of having a genetic disorder. A sample of tissue is obtained such as a sample of tissue or bodily fluid, and nucleic acid PCR amplified, purified or cloned. The target nucleic acid sequence is hybridized to an array of probes, nuclease and polymerase treated and the presence or absence of the genetic defect detected. Disorders which can be detected include, for example, myotonic dystrophy, Huntington's disease, Kennedy disease and Fragile X syndrome. Patients may be any mammal such as a human. Patient samples may be collected and pooled to reduce the number of tests which need to be performed to identify a positive carrier, or sequentially analyzed against a variety of different probe arrays to further limit the number of tests and probes needed.

Another embodiment of the invention is directed to arrays of probes wherein each probe comprises a constant 5'-region, a constant 3'-region and a variable internal region wherein the variable region comprises one or more repeat sequences. The repeat sequence comprises heterologous or homologous sequences which are variable in length or base sequence. Sequences contain purine or pyrimidine bases or neutral bases such as inosine. Either the nucleic acids or the probes of the array may be labeled with a detectable label or fixed to a solid support. Arrays may be spatially ordered by structure or sequence with the sequences of the probes known or determinable. Probes may be single-stranded or partly single-stranded and partly double-stranded. Probes may also be labeled with detectable labels. Arrays may comprise between about 10 to about 10,000 different probes, preferably between about 50 to 5000 different probes, or more or less as required.

The following experiments are offered to illustrate embodiments of the invention, and should not be viewed as limiting the scope of the invention.

EXAMPLES

Example 1
Oligonucleotide Synthesis, Purification, and Characterization

Synthetic oligonucleotides comprising the following sequence were synthesized using an oligonucleotide synthesizer (Operon Technologies, Inc.). The sequences of the oligonucleotides are as follows:

| T1 (78 mer) |
|---|
| 5'-CCAGATCTGA TGCGTCGGAT CATCCAGCAG CAGCAGCAGC AGCAGCAGTC ACGCTAACCG AATCCCTGGT CAGATCTT-3' (SEQ ID NO 1) |

| T2 (78 mer) |
|---|
| 5'-AAGATCTGAC CAGGGATTCG GTTAGCGTGA CTGCTGCTGC TGCTGCTGCT GCTGGATGAT CCGACGCATC AGATCTGG-3' (SEQ ID NO 2) |

| CTG6 (72 mer) |
|---|
| 5'-AAGATCTGAC CAGGGATTCG GTTAGCGTGA CTGCTGCTGC TGCTGCTGGA TGATCCGACG CATCAGATCT GG-3' (SEQ ID NO 3) |

Oligonucleotides T1 and T2 were purified by polyacrylamide gel electrophoresis, while CTG6 was purified by using high performance liquid chromatography. The concentration of each stock solution was determined by absorption at 260 nm.

T1, T2 and CTG6 contain 8 GAC repeats, 8 CTG repeats, 6 CTG repeats, respectively. The GAC repeats are located 30 bases from the 5' end and 24 from the 3' end. The CTG repeats are located 24 from the 5' end and 30 from the 3' end.

Example 2
Determination of S1 Nuclease Specificity and Efficiency

S1 nuclease specificity and efficiency was monitored using 5' radio-labeled oligonucleotides. Briefly, 3.5 µM of oligonucleotide was placed in kinase buffer (70 mM Tris-HCl, pH 7.6, 10 mM $MgCl_2$, 5 mM dithiothreitol) containing 6.4 pM $^{32}$P-ATP (specific activity of 60 Ci/mmole). End labeling was initiated by the addition of 0.35 unit/pmole oligo T4 polynucleotide kinase (New England Biolabs; Beverly, Mass.). Labeling continued for 45 minutes at 37° C. Labeled oligonucleotides were separated from unincorporated $^{32}$P-ATP with a CHROMA-SPIN™+TE 10 columns (Clonetech).

Heteroduplexes were generated by annealing 1 µM of $^{32}$P-labeled oligonucleotide T1 to an equal molar amount of T2 or CT66 in a 50 pL volume of 100 mM Tris-HCl, pH 8.0 (FIG. 1). Oligonucleotides were heated to 96° C. for four minutes and gradually cooled to 30° C. over two hours to ensure specific annealing.

Figure 2B:
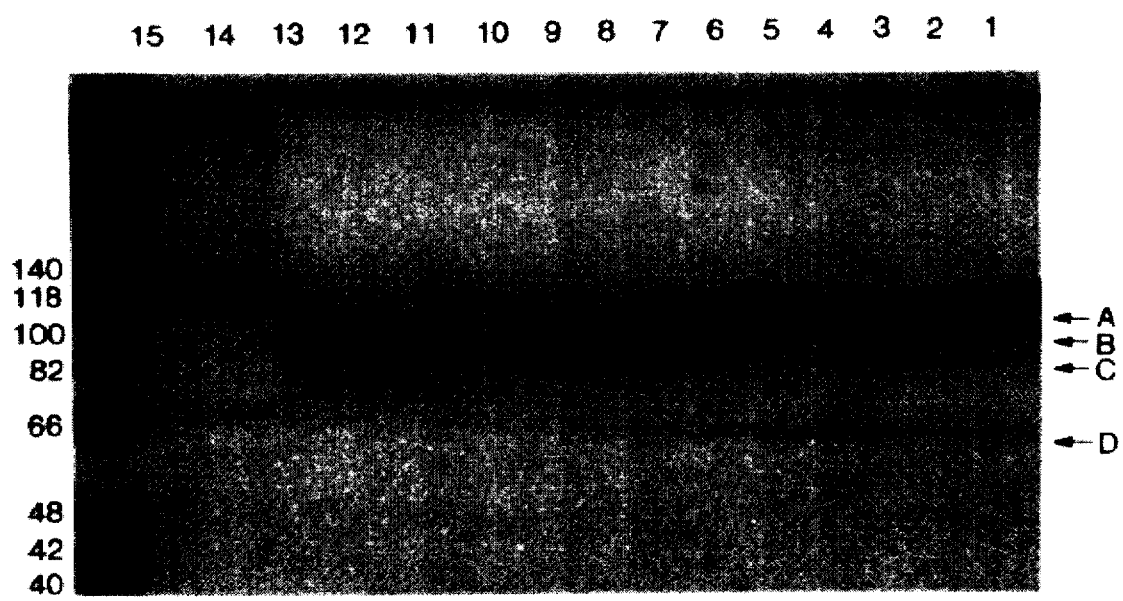
Figure 3A:
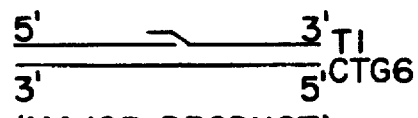
FIG. 3A and B Labeling of S1 cleavage products with radio-labeled nucleotides.
Figure 3A:
Figure 3A:
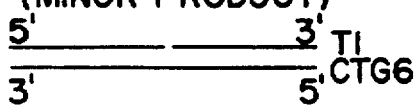
Figure 3A:
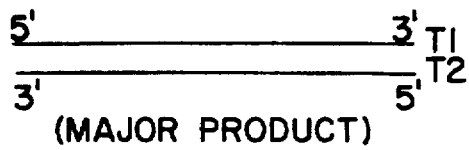
Figure 3A:
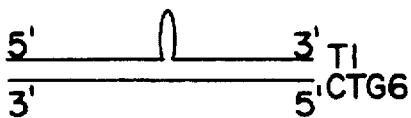
Figure 3B:
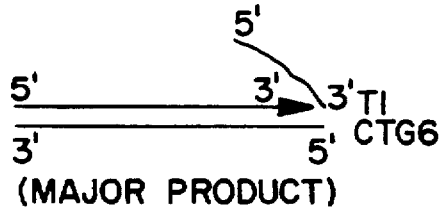
Figure 3B:
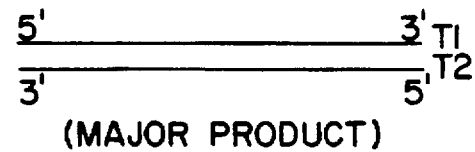
Figure 3B:

The specificity of S1 as a function of enzyme concentration was tested using T1–T2 and T1–CTG6 heteroduplexes labeled as H1 and H2, respectively, in FIG. 1. Briefly, 0.1–1.0 unit/picomole of S1 nuclease (Promega; Madison, Wis.) was added to the heteroduplexes in a solution of 200 mM NaCl, 50 mM sodium acetate, pH 4.5, 1 mM $ZnSO_4$, 0.5% glycerol. Nuclease digestion was performed at temperatures of about 0° C., about 24° C. and about 37° C. The temperatures of the solutions were equilibrated to the reaction temperature before the addition of enzyme. After a reaction period of 60 minutes, further digestion was stopped by the addition of EDTA to a final concentration of 12 mM. Schematics of the expected reaction products are shown in FIG. 1 C. and D. Each reaction product was analyzed by native 12% polyacrylamide gel electrophoresis. Resulting gels were autoradiographed and are depicted in FIGS. 2A and 2B. FIG. 2A depicts an autoradiograph of the reaction product of the perfect match heteroduplex T1–T2. Lane 1 is a minus S1 control. Lanes 2–5 contain increasing concentrations of S1 (0.2, 0.5, 0.8, 1.0 units per picomole oligo) all incubated at 0° C. Lanes 6–9 contain identical concentrations, but were incubated at room temperature, and lanes 10–13 were incubated at 37° C. Although at higher temperatures S1 cut the end label off of the duplex, no other cutting was seen. Lane 0 contains size standard (φX174/ HiinfI digest).

FIG. 2B is an autoradiograph of the reaction product of the mismatched heteroduplex T1-CTG6. Lanes 1–4 contained increasing concentrations of S1 (as above), all incubated at 0° C. Lanes 5–8 follow the same pattern of S1 concentration, but were incubated at room temperature, while lanes 9–12 were incubated at 37° C. Both lanes 13 and 14 contain T1-CTG6 complex without any S1 nuclease. The top band in each lane (band A) matches with the T1-CTG6 control and is just the uncut loop structure. The second band (band B) is the nicked loop, while band C appears to be a nicked loop that has been partially digested. Lane D is very faint, but may contain completely digested loop, leaving a nicked duplex DNA. Lane 15 contains a size standard.

At 0° C., greater than about 60%o of the 6 base loops generated by the mismatched repeats in the T1-CTG6 hybrid complex were cut by S1 nuclease at a concentration of 0.6 units per picomole (FIG. 2). The presence of multiple bands was most likely due to S1 nuclease cleaving the loop structure and thereby degrading several unpaired nucleotides. It also appears that S1 nuclease cut several unpaired nucleotides rather than just one, since distinct bands appeared at separations of more than one base pair. In contrast, no cleavage was seen with the perfectly matched T1-T2 hybrid complex.

At higher temperatures, less of the label appeared in each lane of both the matched and mismatched samples. This was most likely due to S1 nuclease cleaving the breathing ends of duplex DNA as single-stranded structures were formed. This problem was not seen in samples incubated at 0° C. because the extent to which the DNA ends could breath was reduced. These experiments demonstrated that S1 nuclease cleaved the hybrid containing a mismatch at the location of the mismatch.

Example 3
Labeling and Strand Displacement

An enhanced method to discriminate between the matched and mismatched oligonucleotides was examined. Labeling and strand displacement reactions were tested with templates consisting of unlabeled T1-T2 and T1-CTG6 heteroduplexes. Digestion of these duplexes was performed with 0.6 units of S1 nuclease per picomole of oligonucleotide at 0° C. Reactions were terminated and the products purified with a spin column (CHROMA-SPIN™+TE 10). S1 nuclease was inactivated after column purification of the oligonucleotide because of the removal of $ZnSO_4$.

The experimental scheme and the expected results are represented in FIG. 3. The expected digestion products of the mismatched heteroduplex is represented as A1 while the expected digestion product of the perfect match heteroduplex is represented as A2. The expected reaction product after polymerase treatment is shown as B1 and B2, respectively.

Labeling of the S1 digested heteroduplexes were performed for 15 minutes at room temperature with the Klenow fragment of DNA polymerase I. Briefly, 0.08 units per picomole of enzyme was added in a reaction buffer of 50 mM KCl, 10 mM Tris-HCl, pH 8.3, 1.5 mM $MgCl_2$, 0.001% gelatine, 30 pM of each dNTPs, and $^{32}P$-labeled dCTP (specific activity of 1.74 Ci/mmole) in a volume of 50 pl. The reaction was stopped by addition of sodium dodecyl sulfate (SDS) to a final concentration of 0.5%.

Figure 4:
FIG. 4 DNA polymerase radiolabeling of S1 cleaved matched and mismatched substrates.

The product of the labeling reaction was analyzed by acrylamide gel electrophoresis and autoradiography. A copy of the autoradiograph is shown in FIG. 4. Lane 0 is a molecular weight marker. Lane 1 and Lane 2 represents S1 digested and polymerase treated mismatched heteroduplex elongated in the presence (lane 1) and absence (lane 2) of radioactive nucleotide triphosphates. Lane 3 and lane 4 represents S1 digested and polymerase treated perfect match heteroduplex elongated in the presence (lane 3) and absence (lane 4) of radioactive nucleotide triphosphates.

Incorporation of $^{32}P$-labeled of dCMP in the S1-cleaved, mismatched hybrid (T1-CTG6) by Klenow fragment, yielded a strong signal at the position expected if the S1 cleavage occurred at the site of the mismatch (FIG. 4). Only a very weak signal could be detected for the perfectly matched hybrid (T1-T2), and this signal was not localized into any distinct bands. Some non-specific labeling of the perfectly matched hybrid, as well as the T1-CTG6 complex may have arisen from the tendency for S1 nuclease to introduce nicks into double-stranded DNA. However, the loop-cutting activity of S1 nuclease is much stronger than its ability to introduce nicks into perfectly matched double-stranded DNA, which is demonstrated in these experiments.

Example 4
Detection of a Repeated Genomic Sequence

A single-stranded nucleic acid comprising an internal target repeat sequence is generated from genomic DNA for analysis. A schematic of the strategy is shown in FIG. 5. Briefly, one 5'-biotinylated oligonucleotide primer and one non-biotinylated primer is produced using an oligonucleotide synthesizer. The primers flank a region of genomic DNA containing a variable number of repeated nucleotides. A polymerase chain reaction is performed using the two primers and genomic DNA as template (FIG. 5A). Double stranded reaction product is purified from unincorporated nucleotide triphosphates by a size exclusion column. The purified PCR product is denatured in 8M urea and the biotinylated strand removed. The non-biotinylated strand is labeled at the 3' end with a fluorescein and used as the target nucleic acid.

A plurality of probes, each containing 5' and a 3' sequence complementary to the target nucleic acid and from 10 to 109 internal repeats are synthesized on an oligonucleotide synthesizer. Probes of 80 bases or shorter are synthesized and used directly. Probes greater than 80 bases in size are synthesized as fragments and ligated together. After generation, probes are labeled at the 3' terminus with rhodamine. All the probes are synthesized with a 5' biotin and these biotinylated probes are attached to the bottom of a plate coated with immobilized streptavidin. Probes are attached along a 10×10 array and ordered according to size (FIG. 5B).

Target nucleic acid is hybridized to the probe array (FIG. 5C) and digested with S1 nuclease (FIG. 5D). DNA polymerase is added to the array and elongation and strand displacement is allowed to occur (FIG. 5E) until completion (FIG. 5F). When the probe contains more internal repeats than the target, the rhodamine label will be lost in the strand displacement and the resultant product will be red. Similarly, when the target contains more internal repeats than the probe, the fluorescein label will be lost and the product will be green. When the probe and the target both contain the same number of repeats, both rhodamine and fluorescein will remain and the resultant color will be yellow.

Figure 6A:
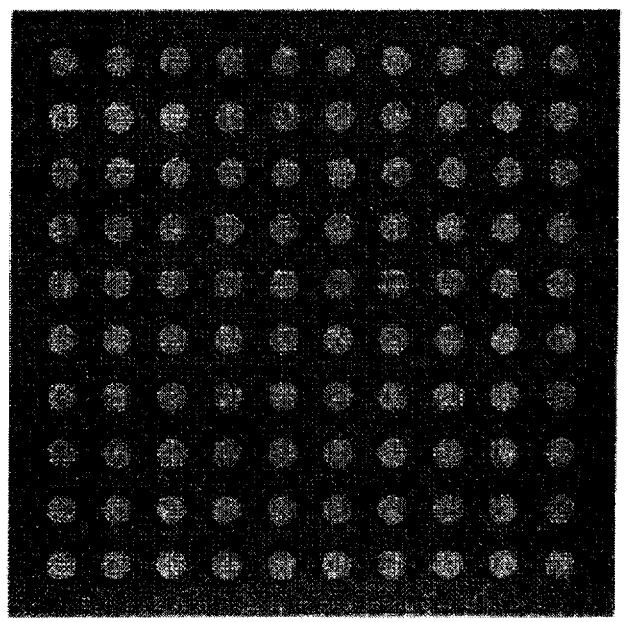
FIG. 6 Two dimensional array for the detection of between 10 to 109 repeats.
Figure 6B:
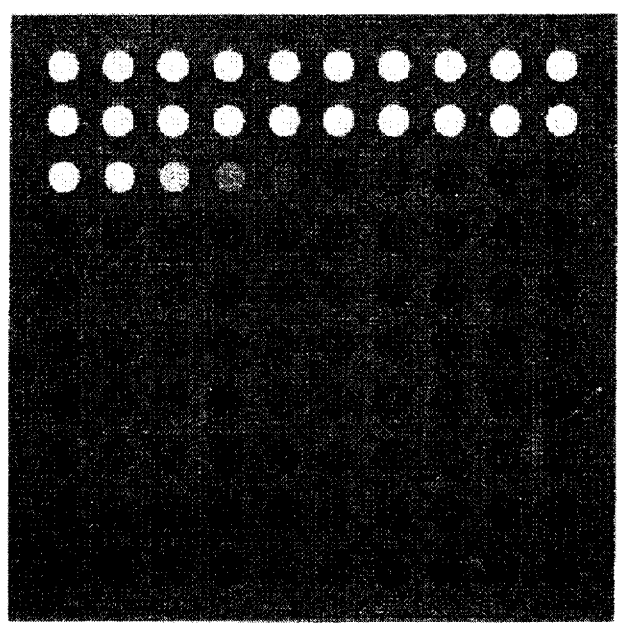
Figure 6C:
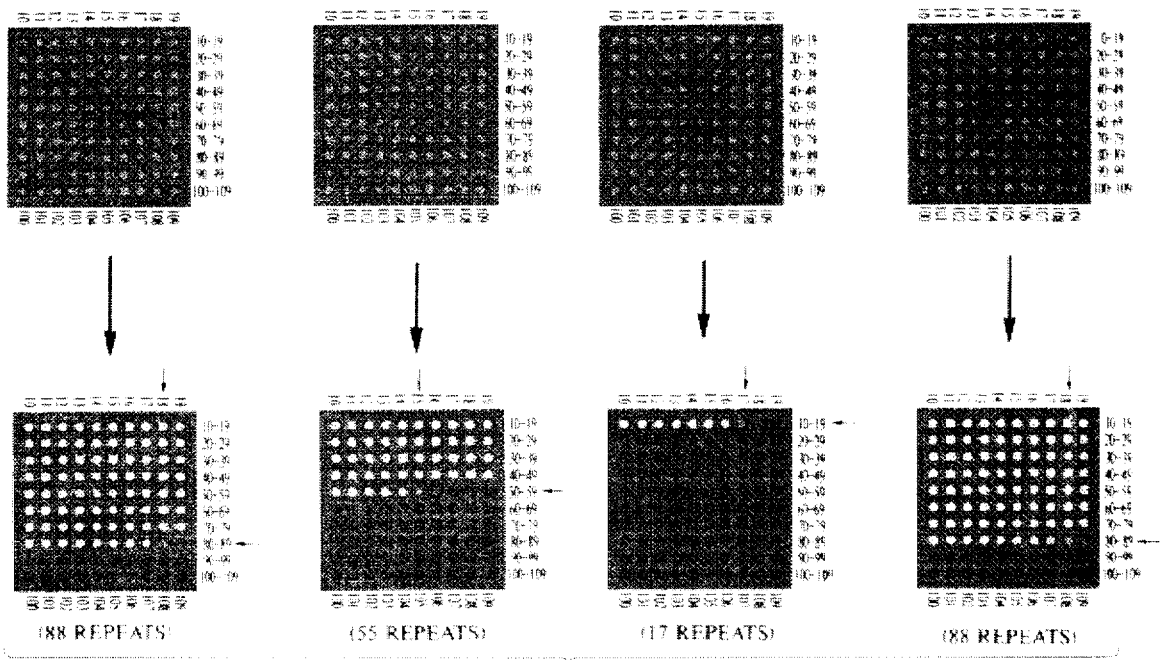

After strand displacement the array is inspected visually. The result is displayed in FIG. 6. All the probes are yellow before strand displacement (FIG. 6A). After S1 cutting and strand displacement, the probes with fewer repeats than the target is red and the probe with more repeats is green. The probe with the same number of repeat is yellow. The results of experiments performed with the same probe array but with target DNA comprising 88, 55, and 17 repeats are shown in FIG. 6B. This experiment demonstrates how a colormetric assay may be performed to determine the number of repeats in a target sequence.

Example 5
Detection of Repeated Sequence from Myotonic Dystrophy Patient

To determine the extent of expansion of trinucleotide repeat in a myotonic patient, a 5 ml sample of blood is drawn from the patient for analysis. Whole cell DNA is isolated from the blood and a DNA, comprising a region of trinucleotide repeats, implicated as a cause for myotonic dystrophy disorder, is amplified and isolated by polymerase chain reaction. Polymerase chain reaction products are denatured and one of the DNA strands used as the nucleic acid containing the target sequence to be detected.

An oligonucleotide synthesizer is used to generate a set of oligonucleotide probes. Each probe in the set has a 20 base-pair 5' sequence and a 20 base-pair 3' sequence complementary to the sequence flanking the trinucleotide repeat region. In addition, each probe in the set has an internal trinucleotide repeat between the 5' and 3' sequence. A series of 20 probes are synthesized containing from 1 to 20 trinucleotide repeats.

Three picomoles of each probe, a total of 60 picomoles, is hybridized to 200 pmoles of the amplified target nucleic acid. Briefly, the probes and the targets are heated in 100 mM Tris-HCl, pH 7.5, 50 mM NaCl, to 96° C. for four minutes and cooled gradually to 30° C. over two hours to ensure specific annealing to form heteroduplex with mismatches and perfect matches. Heteroduplexes are treated with 0.3 unit per picomole of S1 nuclease at 0° C. for 5 minutes. The reaction is stopped by chromatography of the reaction mixture through a spin column.

Polymerase treatment of the S1 digested heteroduplexes is performed for 15 minutes at room temperature with the Klenow fragment of DNA polymerase I. Briefly, 0.08 units of enzyme is added per picomole DNA in a reaction buffer of 50 mM KCl, 10 mM Tris-HCl, pH 8.3, 1.5 mM $MgCl_2$, 0.001% gelatine, 30 pM of each dNTPs. The reaction is stopped by addition of sodium dodecyl sulfate (SDS) to a final concentration of 0.5%.

The product of this reaction is analyzed on a denaturing sequencing gel with the set of DNA probes as a molecular weight marker. After electrophoresis, the gel is treated with water for 30 minutes to remove the urea and stained with SBYR or FBIR. Bands are detected upon exposure to ultraviolet light. The largest product observed is a 61 base band corresponding to 7 trinucleotide repeats.

Other embodiments and uses of the invention will be apparent to those skilled in the art from consideration of the specification and practice of the invention disclosed herein. All U.S. Patents cited herein are specifically incorporated by reference. The specification and examples should be considered exemplary only with the true scope and spirit of the invention indicated by the following claims.

We claim:

1. A method for detecting a target sequence within a nucleic acid comprising the steps of:
   a) hybridizing the nucleic acid to an array of probes wherein each probe comprises a 5'-region complementary to the 3'-region of said nucleic acid, a 3'-region complementary to the 5'-region of said nucleic acid and an internal variable region which is unique to each probe to form a hybridized array;
   b) digesting the hybridized array with a single-strand specific nuclease;
   c) treating said array with a nucleic acid polymerase; and
   d) identifying a probe with an internal variable region complementary to the target sequence.

2. The method of claim 1 wherein the target sequence and the internal variable region of each probe comprise a plurality of repeat sequences.

3. The method of claim 2 wherein the plurality comprises between about 2 to about 2000 repeat sequences.

4. The method of claim 2 wherein the repeat sequences are each between about 2 to about 25 nucleotides in length.

5. The method of claim 1 wherein the nucleic acid is DNA, RNA, PNA or modifications thereof.

6. The method of claim 1 wherein the nucleic acid is labeled at a 5'-terminus or a 3'-terminus with a chemical moiety.

7. The method of claim 6 wherein the chemical moiety is selected from the group consisting of radioisotope, stable isotopes, luminescent and electroluminescent chemicals, fluorescent chemicals, chromogenic chemicals, metals, coupling agents and magnetic agents.

8. The method of claim 1 wherein the nucleic acid is from a biological sample.

9. The method of claim 8 wherein the biological sample is a sample of biomass, bodily tissue, bodily fluid or combination thereof.

10. The method of claim 1 wherein the nucleic acid is a polymerase chain reaction product.

11. The method of claim 1 wherein the 5'-region and the 3'-region are each between about 15 to about 100 nucleotides in length.

12. The method of claim 1 wherein the variable region comprises a plurality of repeat sequences.

13. The method of claim 12 wherein the plurality comprises between about 2 to about 2000 repeat sequences.

14. The method of claim 13 wherein the repeat sequences are each between about 2 to about 25 nucleotides in length.

15. The method of claim 1 wherein the variable region is variable in sequence or length.

16. The method of claim 15 wherein the length is between about 10 to about 2000 nucleotides.

17. The method of claim 1 wherein the variable region comprises a sequence of neutral bases.

18. The method of claim 17 wherein the neutral bases are inosine bases.

19. The method of claim 1 wherein the nucleic acid is labeled at a 5'-terminus or a 3'-terminus with a chemical moiety.

20. The method of claim 19 wherein the chemical moiety is selected from the group consisting of radioisotope, stable isotopes, fluorescent chemicals, luminescent and electroluminescent chemicals, chromogenic chemicals, metals, coupling agents and magnetic agents.

21. The method of claim 1 wherein the nucleic acid and the probes are labeled with different chromogenic chemicals.

22. The method of claim 1 wherein the array is fixed to a solid support.

23. The method of claim 22 wherein the solid support is selected from the group consisting of plastics, glasses, ceramics, metals, resins, gels, membranes, chips and combinations thereof.

24. The method of claim 1 wherein the single-strand specific nuclease is S1 nuclease, mung bean nuclease, ribonuclease A or ribonuclease T1.

25. The method of claim 1 wherein the nucleic acid polymerase is a DNA polymerase, a reverse transcriptase, an RNA polymerase or a thermostable polymerase.

26. The method of claim 1 wherein the target sequence detected is indicative of a disorder.

27. The method of claim 1 wherein the disorder is myotonic dystrophy, Huntington's disease, Kennedy disease or Fragile X syndrome.

28. A method for determining a length of a target sequence within a nucleic acid comprising the steps of:

a) hybridizing the nucleic acid to an array of probes wherein each probe comprises a 5'-region complementary to the 3'-region of said nucleic acid, a 3'-region complementary to the 5'-region of said nucleic acid, and an internal variable region which is unique to each probe to form a hybridized array;

b) digesting the hybridized array with a single-strand specific nuclease;

c) treating said array with a nucleic acid polymerase; and d) determining the length of the target sequence.

29. The method of claim 28 wherein the nucleic acid is a PCR product.

30. The method of claim 28 wherein the internal variable region comprises a plurality of contiguous identical bases.

31. The method of claim 30 wherein the plurality of contiguous identical bases are inosine residues or modifications of inosine residues.

32. A method for determining the number of repeat sequences within a target sequence of a nucleic acid comprising the steps of:

a) hybridizing the nucleic acid to an array of probes wherein each probe comprises a 5'-region complementary to the 3'-region of said nucleic acid, a 3'-region complementary to the 5'-region of said nucleic acid and an internal region containing one or more repeat sequences which is unique to each probe to form a hybridized array;

b) digesting the hybridized array with a single-strand specific nuclease;

c) treating said array with a nucleic acid polymerase; and d) identifying a probe containing an internal variable region complementary to the target sequence and determining the number of repeat sequences within the target sequence.

33. The method of claim 32 wherein the nucleic acid is from a mammal, an insect or a microorganism.

34. The method of claim 32 wherein the array comprises greater than R different probes and R is the number of repeat sequences in the target sequence.

35. The method of claim 32 wherein the array comprises a fraction of R probes and R is the number of repeats in the target sequence.

36. The method of claim 35 wherein the steps a, b, and c are repeated using a different fraction of the array.

37. The method of claim 32 wherein the internal region is between about 10 to about 2000 nucleotides in length.

38. The method of claim 32 wherein the repeat sequences are each between about 2 to about 10 nucleotides in length.

39. The method of claim 32 wherein the repeat sequences are contiguous.

40. The method of claim 32 wherein the variable region comprises a sequence of neutral bases.

41. The method of claim 32 further comprising the step of pooling a collection of different nucleic acids and hybridizing the collection to the array.

42. A method for screening a patient suspected of having a genetic disorder characterized by the presence or absence of a target repeat sequence comprising the steps of:

a) amplifying a nucleic acid from a patient sample;

b) hybridizing said nucleic acid to an array of probes wherein each probe comprises a 5'-region complementary to the 3'-region of said nucleic acid, a 3'-region complementary to the 5'-region of said nucleic acid and an internal variable region which is unique to each probe to form a hybridized array;

c) digesting the hybridized array with a single-strand specific nuclease;

d) treating said array with a nucleic acid polymerase; and e) identifying a probe containing an internal variable region complementary to the target repeat sequence and detecting the presence or absence of the genetic disorder.

43. The method of claim 42 wherein the patient is a mammal.

44. The method of claim 43 wherein the mammal is a human.

45. The method of claim 42 wherein the genetic disorder is myotonic dystrophy, Huntington's disease, Kennedy disease or Fragile X syndrome.

46. The method of claim 42 wherein the nucleic acid is amplified by polymerse chain reaction.

47. The method of claim 42 further comprising the step of pooling a collection of nucleic acids from different patients, hybridizing the collection to the array and determiinig the presence or absence of the genetic disorder in any of the patients.

48. An array of at least 10 probes wherein each probe comprises an identical 5'-region, an identical 3'-region and a variable internal region wherein said variable region comprises one or more repeat sequences which is unique to each probe.

49. The array of claim 48 wherein the repeat sequence comprises a sequence of inosine residues.

50. The array of claim 48 which comprises between about 50 to about 5000 different probes.

51. The array of claim 48 which comprises greater than 5000 different probes.

52. The array of claim 48 which comprises DNA, RNA, PNA or modifications thereof.

53. The array of claim 48 wherein the probes are labeled with a detectable label.

54. The array of claim 53 wherein the detectable label is a chromagenic chemical.

55. The array of claim 48 which is fixed to a solid support.

56. The method of claim 1 wherein the probes are fixed at discrete sites to a solid support.

57. The method of claim 40, wherein the neutral bases are inosine residues or modifications of inosine residues.

58. The method of claim 57 wherein the probes of the array are hybridized to the fixed nucleic acids sequentially.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
CCAGATCTGA TGCGTCGGAT CATCCAGCAG CAGCAGCAGC AGCAGCAGTC ACGCTAACCG        60

AATCCCTGGT CAGATCTT                                                    78
```

( 2 ) INFORMATION FOR SEQ ID NO:2:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO

```
        ( i v ) ANTI-SENSE: NO ( v ) FRAGMENT TYPE:

( v i ) ORIGINAL SOURCE:

( x i ) SEQUENCE DESCRIPTION: SEQ ID NO:2:

AAGATCTGAC CAGGGATTCG GTTAGCGTGA CTGCTGCTGC TGCTGCTGCT GCTGGATGAT        60

CCGACGCATC AGATCTGG                                                     78

( 2 ) INFORMATION FOR SEQ ID NO:3:

( i ) SEQUENCE CHARACTERISTICS:
                ( A ) LENGTH: 72 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

AAGATCTGAC CAGGGATTCG GTTAGCGTGA CTGCTGCTGC TGCTGCTGGA TGATCCGACG        60

CATCAGATCT GG                                                           72
```